United States Patent [19]

Kilbourn et al.

[11] 4,033,972

[45] July 5, 1977

[54] 3-PYRIDYLMETHYL-(N-SUBSTITUTED PHENYL)-CARBAMATE DERIVATIVES

[75] Inventors: Edward E. Kilbourn, Chalfont; Ernest D. Weiler, Ambler, both of Pa.

[73] Assignee: Rohm and Haas Company, Philadelphia, Pa.

[22] Filed: Sept. 9, 1975

[21] Appl. No.: 611,759

Related U.S. Application Data

[62] Division of Ser. No. 497,542, Aug. 14, 1974, Pat. No. 3,925,397.

[52] U.S. Cl. .............. 260/294.8 D; 260/294.8 G; 260/294.9; 260/295.5 C; 424/84
[51] Int. Cl.$^2$ .............. C07D 417/12; C07D 213/46
[58] Field of Search .............. 260/295.5 C, 294.8 D, 260/294.9, 294.8 G

[56] References Cited

UNITED STATES PATENTS 3,931,202  1/1976  Ware et al. ................ 260/294.8 F Primary Examiner—Alan L. Rotman

[57] ABSTRACT

3-Pyridylmethyl-(N-substituted-phenyl-N-hydrocarbyl)carbamates.
They are useful as rodenticides.

6 Claims, No Drawings

3-PYRIDYLMETHYL-(N-SUBSTITUTED PHENYL)-CARBAMATE DERIVATIVES

This is a division, of application Ser. No. 497,542 filed Aug. 14, 1974, now U.S. Pat. No. 3,925,397 granted Dec. 9, 1975.

The present invention relates to 3-pyridylmethyl N-cyano-(or methylmercapto or nitro)phenyl-N-alkyl-(or allyl or benzyl or 2-thenyl)carbamates. They are useful for the control and extermination of pest rodents. This includes their salts and metal salt complexes since these derivatives retain the rodenticidal properties of the parent pyridine derivative and are considered synonymous with them.

Each 3-pyridylmethyl (N-substituted-phenyl-N-hydrocarbyl)carbamate of this invention or its salt derivatives is a very effective single-dose rodenticide and yet is relatively safe for use as a rodenticide in the presence of animal species, other than rodents, which could inadvertently ingest limited quantities of the compound.

The common rat, Rattus norvegicus, is vicious and constantly poses a serious threat to the health and well being of man. Rats and mice are destructive animals and a serious nuisance, causing millions of dollars damage annually to farms, agronomic crops, homes, food processing plants and many other businesses. Rats bite at least 14,000 (possibly up to 60,000) people every year, according to the U.S. Public Health Service and are known carriers of over 35 contagious diseases including bubonic plague, trichinosis, typhus, rat bite fever, amoebic dysentery, tuberculosis, infectious jaundice and rabies. During the years from 1898 to 1923, almost 11 million deaths were caused by rat-borne plagues.

Use of rodenticides, fumigants, sprays and traps are the primary methods employed for the control of pest rodents. The term "pest rodents" refers not only to members of the order Rodentia but also to those of lagomorpha, which cause health hazards or economic loss unless kept in check. Rodenticides may be used in the form of a tracking powder or a bait or may be applied as a spray on the rodent's natural foodstuffs. The rodenticides used as a bait are of two classes: single and multi-dose. Multi-dose rodenticides are usually selected over single-dose rodenticides, as they have been safer in the past than the available single-dose rodenticides. The multi-dose rodenticides are anti-coagulants, including a number of different 4-hydroxycoumarin and 1,3-indandione compounds. These multi-dose rodenticides consumed in small daily amounts have a lethal effect on rats and mice after liver stores of vitamin K have been depleted. Anti-coagulants are less effective on mice than rats, as mice are considered to be nibblers and may not consume an adequate amount of treated bait to have a lethal effect. A single-dose rodenticide which would be relatively safe to the person handling the material and to non-target species of animals and yet effective on a variety of pest rodents is highly desirable.

Many compounds are toxic to rodents. However, very few of these compounds are anywhere near suitable for use as a rodenticide because it is necessary for the pest rodent to consume voluntarily a sufficient amount of the poison even through sufficient untreated food may also be available. In bait rodenticides, feed acceptance is the key to excellence, and in all rodenticides safety and efficacy are highly important.

3-Pyridylmethyl N-[4-cyano-(or methylmercapto-or nitro-)phenyl]-carbamates are known rodenticides, e.g. see Belgium Pat. No. 796,753.

The structural requirements, however, for excellent rodenticidal activity for this class of carbamates is quite exacting and unpredictable. This is particularly true for such carbamates having two substituents on the carbamate nitrogen. Normally only single substitution on this nitrogen with an N-substituted-phenyl group is tolerated.

The basic compounds of this invention have the formula:

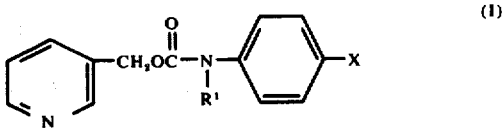

wherein X is cyano, methylthio or nitro and $R^1$ is alkyl of 1 to 4 carbon atoms, allyl, benzyl or 2-thenyl.

Several methods for preparing compounds similar to those of this invention are described in British Patent 1,132,988 and methods b), c), d) and e) on page 2 therein may be used for the present compounds. Method b) is preferred and is depicted below using a carbamoyl chloride as the carbamoyl compound intermediate.

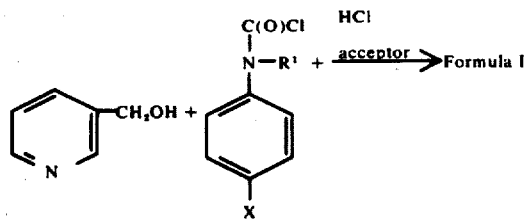

This type reaction has been referred to as carbamoylation.

The carbamoylation type reaction illustrated above is carried out in the presence of an inert solvent such as an aromatic hydrocarbon, an ether, a chlorinated hydrocarbon such as chloroform, and pyridine. The reaction proceeds at room temperature and is accelerated by warming up to the boiling point of the solvent. The condensing agent (HCl acceptor) is a basic substance which will not decompose the carbamate products, and is most commonly a tertiary amine such as triethylamine. In some instances the starting 3-pyridyl carbinol is converted to its sodium alkoxide derivative, e.g. by means of sodium hydride, which then is reacted with the carbamoyl halide.

The following examples describe variations in the preparation of the compounds of the present invention.

EXAMPLE 1

Preparation of 3-pyridylmethyl N-methyl-N-(4-cyanophenyl)carbamate

To a solution of 3-pyridylcarbinol (4.3g., 0.0392 mole) in 200 ml. of ethylene glycol monomethyl ether (glyme) was added a 57% dispersion of sodium hydride in oil (1.7g., 0.0392 mole). After the exothermic reaction had subsided and the evolution of hydrogen had ceased, a solution of N-methyl-N-(4-cyanophenyl)carbamoyl chloride in 30 ml. of glyme was added dropwise. A suspension formed and was stirred at room temperature for 18 hrs. The reaction mixture was poured into 700 ml. of water. The reaction product was extracted with methylene dichloride and the extract was dried over magnesium sulfate and concentrated. The residue was an oil which solidified. This was recrystallized from hexane to give 1.5g. of solid melting at 82°–84.5° C. This solid is a 14.4% yield of 3-pyridylmethyl N-methyl-N-(4-cyanophenyl)carbamate.

EXAMPLE 2

Preparation of 3-pyridylmethyl N-methyl-N-(4-methylthiophenyl)carbamate

A solution of 3-pyridylcarbinol (2.4g., 0.0222 mole) in triethylamine (2.24g., 0.0222 mole) was added dropwise to a solution of N-methyl-(4-methylthiophenyl)-carbamoyl chloride in 150 ml. of benzene. The reaction mixture was heated to reflux temperature for about 1 hr. then allowed to stand over night at room temperature. The reaction mixture was washed with water and the benzene layer separated, dried over magnesium sulfate and concentrated in vacuo to give an oil which solidified. The product was recrystallized from methylcyclohexane to give 2.6g. of solid melting at 100°–102° C. This was a 40.5% yield of 3-pyridylmethyl N-methyl-N-(4-methylthiophenyl)carbamate.

Tables I and II give the description and analytical data for typical examples of this invention.

Table I

| Example | $R^1$ | X | Melting Point (° C) |
|---|---|---|---|
| 1 | $CH_3$ | CN | 82–84.5 |
| 2 | $CH_3$ | $-SCH_3$ | 100–102 |
| 3 | $CH_3$ | $NO_2$ | 108–111 |
| 4 | $C_4H_9$-n | CN | 78.5–81.5 |
| 5 | $C_4H_9$-n | $NO_2$ | oil |
| 6 | $-CH_2CH=CH_2$ | CN | 52–56 |
| 7 | $-CH_2CH=CH_2$ | $NO_2$ | oil |
| 8 | $-CH_2C_6H_5$ | CN | 108–110 |
| 9 | $-CH_2C_6H_5$ | $-SCH_3$ | oil |
| 10 | $-CH_2C_6H_5$ | $NO_2$ | oil |
| 11 | $-CH_2$-(2-thienyl) | $NO_2$ | oil |
| Prep. A | $C_8H_{17}$-n | $NO_2$ | oil |

Table II

Analytical Data on Examples

| Example | Empirical Formula | C | H | N |
|---|---|---|---|---|
| 1 | $C_{15}H_{13}N_3O_2$ | 66.9(67.4) | 4.8(4.9) | 15.5(15.7) |
| 2 | $C_{15}H_{16}N_2O_2S$ | 62.5(62.5) | 5.7(5.6) | 9.8( 9.7) |
| 3 | $C_{14}H_{13}N_3O_4$ | 58.5(58.5) | 4.7(4.6) | 14.9(14.6) |
| 4 | $C_{18}H_{19}N_3O_2$ | 69.7(69.9) | 6.1(6.2) | 13.8(13.6) |
| 5 | $C_{17}H_{19}N_3O_4$ | 61.6(62.0) | 5.9(5.8) | 12.7(12.8) |
| 6 | $C_{17}H_{15}N_3O_2$ | 69.8(69.6) | 5.5(5.2) | 14.4(14.3) |
| 7 | $C_{16}H_{15}N_3O_4$ | 61.2(61.3) | 5.0(5.8) | 13.2(13.4) |
| 8 | $C_{21}H_{17}N_3O_2$ | 73.3(73.7) | 5.2(5.0) | 12.1(12.2) |
| 9 | $C_{21}H_{20}N_2O_2S$ | 68.8(69.2) | 5.7(5.5) | 7.9( 7.7) |
| 10 | $C_{20}H_{17}N_3O_4$ | ** | ** | |
| 11 | $C_{18}H_{15}N_3O_4S$ | ** | ** | |

*The value in parentheses is that calculated from the empirical formula.
**The identity of these products was established through their nmr and infrared spectra and by thin layer chromatography which established that only one component was present.

The 3-pyridylcarbinol intermediate is a product of commerce. The intermediate N-(hydrocarbyl)-N-(p-substituted-phenyl)carbamoyl chlorides were made by the well-known reaction of the secondary amine with phosgene in an inert solvent at room temperature. A typical reference for this general reaction is Slocombe et al. J. Am. Chem. Soc. 72, 1888 (1970). In every case the infrared spectrum showed the presence of the carbonyl group. The following table gives pertinent data for the carbamoyl chlorides used in this invention, all of which are novel compounds.

Table III

Carbamoyl Chloride Intermediates

| Used in Example | $R^1$ | X | Yield (%) |
|---|---|---|---|
| 1 | methyl | CN | 86 |
| 2 | methyl | $-SCH_3$ | 100 |
| 3 | methyl | $NO_2$ | 85 |
| 4 | n-butyl | CN | 99 |
| 5 | n-butyl | $NO_2$ | 100 |
| 6 | allyl | CN | 100+ |
| 7 | allyl | $NO_2$ | 100 |
| 8 | benzyl | CN | 86 |
| 9 | benzyl | $-SCH_3$ | 87 |
| 10 | benzyl | $NO_2$ | 99 |
| 11 | 2-thenyl | $NO_2$ | 100 |
| Prep. A | n-octyl | $NO_2$ | 100 |

The carbamates of this invention can be converted to novel acid salts with a strong inorganic or organic acid. Typical strong acids include hydrobromic, hydrochloric, hydrofluoric, nitric, phosphoric, sulfuric, chloroacetic, oxalic, maleic, succinic and p-toluenesulfonic.

The carbamates of this invention react with metal salts in solution to give metal salt complexes. Typical salts which react in this manner are calcium, cobaltous, cupric, manganous and zinc bromides, chlorides, nitrates, sulfates, acetates and oxalates.

The 3-pyridylmethyl carbamates of the present invention may be formulated into rodenticidal compositions such as baits, tracking powders, and sprays. A bait comprises a semi-moist or dry edible carrier and the toxicant. The dry carrier is generally preferred and may be a combination of natural food products such as whole ground corn, steel cut oats, sugar, molasses, rice, vegetable oil, salt, dehydrated fruit, fish meal, tankage or wheat. When necessary to use in damp locations, the matrix may be a water repellent material such as paraffin wax or an acrylic polymer.

The compounds of the present invention may be incorporated as a toxicant in bait formulations, either alone or in combination with other toxicants. When used as the sole toxicant in baits the compounds of the present invention may be used in any rodenticidally effective concentration.

Depending on the susceptibility of the rodents to the toxicant and the amount of formulated bait generally consumed, concentrations as low as 0.1 may be employed. A typical bait usually contains between about 0.5 and 1.5% of the toxicant by weight but can contain from 0.1 to 99.5% of the toxicant. Rats, mice and other rodents accept the compounds of the present invention quite well when offered free choice between the untreated basal ration and a bait containng one of the compounds of this invention. An example below describes the formulation of a suitable bait, although wide variations in formulation for different conditions of use are of course expected.

BAIT FORMULATION

A 3-pyridylmethyl carbamate of this invention was blended with the basal ration in a Waring laboratory blender to form 50 grams of a homogeneous premix. The amount of compound utilized was determined by the percentage of active material desired in the feed. The formula for the basal ration is shown below, all percentages being by weight:

Crude ground corn 65%
Steel cut oats 25%
Powdered sugar 5%
Corn oil 5%

The 50 grams of premix containing the toxicant were then mixed with an additional 450 grams of basal ration. These components were mixed in a Little Ford Lodge mixer for three minutes.

Tracking powders, which are particularly effective against mice, may be either a compound of the present invention in finely powdered form or a mixture of the compound with powdered carrier, e.g., talc, sugar, milk powder, Indian corn meal, fish meal, cornstarch, flour, and bentonite, or the like or any combination thereof which tends to induce the animals contaminated with the preparation to lick themselves more thoroughly. In tracking powders, a compound of the present invention may be incorporated in amounts from 100% down to 0.1% by weight with proper formulation. An example below describes the preparation of a suitable tracking powder.

TRACKING POWDER

The active compound is finely pulverized by mortar and pestle to form a 100% active tracking powder. To form a 5% active material, it may be mixed with 10X confectioner's sugar in a 1 to 19 ratio and at other ratios for other levels of active compound.

The compounds were preliminarily evaluated for their ability to kill albino rats (*Rattus norvegicus*) by oral administration to two rats at a dosage of 50 mg./kg. or more. In the standard test the effect on the rats is observed over a 14 day period. Table IV, Part A, gives the results with typical examples of this invention. In this table the time given in parentheses indicates when the last rat died.

One of the most significant secondary tests is a standard one known as the paired-preference test. In this test the rodents are given a free choice between the treated and untreated bait in individual cages or in a communal tank. Such a test most nearly approximates practical use conditions.

When caged individually, they were provided with dual feed cups and separate water devices. When caged in a communal tank, they were offered a multiplicity of feed cups and water devices. The basal ration was offered in excess of daily feed requirements in each of two feeders; one treated with the test compound and one without. For each test, equal numbers of each sex were used.

The gross weight of each feed container and its feed were determined daily and returned to the starting weight by addition of complete replacement of the given diet. The position of the bait and the laboratory diet cups in the cage were reversed every 24 hours to counter any feeding position habit of the rat. The test rodents had free choice between treated and untreated feed. Mortalities were recorded daily.

To meet the criteria for a single-dose product, a rodenticide in this initial test must kill 75% of the rats within 8 days, where the poison bait is available for the first 72 hours of this period.

The results of representative paired preference tests with several dosage levels on individually caged rodents are given in Table IV, Part B.

Table IV

| | Rodenticidal Data | | |
|---|---|---|---|
| A. Oral toxicity Example | Dosage (mg./kg.) | Mortality No. dead / Total No. | |
| 1 | 50 | 1/2 | (5 days) |
| | 200 | 2/2 | (20 hrs.) |
| 2 | 50 | 2/2 | (5 hrs.) |
| 3 | 50 | 2/2 | (18 hrs.) |
| 4 | 50 | 2/2 | (5 hrs.) |
| 5 | 200 | 2/2 | (2 hrs.) |
| 6 | 200 | 2/2 | (7 days) |
| 7 | 50 | 2/2 | (18 hrs.) |
| 8 | 200 | 2/2 | (24 hrs.) |
| 9 | 200 | 2/2 | (24 hrs.) |
| 10 | 80 | 2/2 | (3 hrs.) |
| 11 | 50 | 2/2 | (3 hrs.) |
| | 200 | 2/2 | (3 hrs.) |
| Prep. A | 200 | 0/2 | |

| B. Paired preference tests | | | |
|---|---|---|---|
| Example | Rodent | Compound in Basal Ration (ppm) | Mortality No. dead/Total No. |
| 2 | Albino rat | 10,000 | 1/2 |
| 3 | Albino rat | 10,000 | 2/2 |
| | Norway rat | 20,000 | 1/2 |
| 4 | Albino rat | 10,000 | 0/2 |

We claim:
1. A compound of the formula

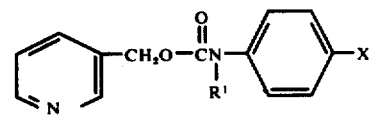

where
X is cyano, methylthio, or nitro; and
R¹ is 2-thenyl when X is cyano or nitro; and when X is methylthio, R¹ is allyl, benzyl or 2-thenyl.

2. A compound according to claim 1 wherein R¹ is allyl.

3. A compound according to claim 1 wherein R¹ is benzyl.

4. A compound according to claim 1 wherein R¹ is 2-thenyl.

5. A compound according to claim 1 wherein X is methylthio.

6. A compound according to claim 1 wherein X is cyano or nitro and R¹ is 2-thenyl.

* * * * *